United States Patent [19]

Jung

[11] 4,434,231

[45] Feb. 28, 1984

[54] MEANS FOR EMBEDDING MICROORGANISMS IN A POLYMER MATRIX

[75] Inventor: Gerard Jung, Montlhery, France

[73] Assignee: Rhone-Poulenc Industries, Paris, France

[21] Appl. No.: 293,441

[22] Filed: Aug. 14, 1981

Related U.S. Application Data

[63] Continuation of Ser. No. 136,329, Apr. 1, 1980, abandoned.

[30] Foreign Application Priority Data

Apr. 5, 1979 [FR] France .............................. 79 08597

[51] Int. Cl.$^3$ ............................................. C12N 1/20
[52] U.S. Cl. ...................................... 435/253; 435/180; 435/260; 435/878; 71/7; 47/57.6
[58] Field of Search ............... 47/57.6; 71/6, 7, 64.08, 71/64.09, 64.10, 27; 435/178–181, 260, 253, 254, 878; 106/205

[56] References Cited

U.S. PATENT DOCUMENTS

| | | | |
|---|---|---|---|
| 2,901,864 | 9/1959 | Hiler | 47/58 |
| 2,988,455 | 6/1961 | Rosenberg et al. | 106/169 |
| 2,995,867 | 8/1961 | Burton | 71/7 |
| 3,168,796 | 2/1965 | Scott et al. | 435/260 |
| 3,472,644 | 10/1969 | Woodside | 71/6 |
| 3,765,918 | 10/1973 | Jordan et al. | 106/205 |
| 3,898,132 | 8/1975 | Hettrick | 71/6 |
| 4,038,140 | 7/1977 | Jaworek et al. | 195/63 |
| 4,089,746 | 5/1978 | Masri et al. | 195/63 |
| 4,155,737 | 5/1979 | Dommergues et al. | 71/7 |
| 4,202,905 | 5/1980 | Asai et al. | 435/178 |

FOREIGN PATENT DOCUMENTS 977178 11/1975 Canada ................................ 71/16

*Primary Examiner*—Ferris H. Lander
*Attorney, Agent, or Firm*—Herbert F. Schwartz; James F. Haley, Jr.; Eugene S. Indyk

[57] ABSTRACT

Novel processes are provided for the embedding of microorganisms within a polymer matrix wherein the matrix comprises a polymer gel having a base of at least one polymer selected from the group of polysaccharides, in which said polymer is at least partially crosslinked. The embedded microorganism products are useful in the inoculation of leguminous and non-leguminous plants in order to increase their nitrogen-fixing potential and nutrition, respectively.

18 Claims, No Drawings

MEANS FOR EMBEDDING MICROORGANISMS IN A POLYMER MATRIX

This is a continuation, of application Ser. No. 136,329, filed Apr. 1, 1980, and now abandoned.

BACKGROUND OF THE INVENTION

The present invention relates to a new means for embedding microorganisms within a polymer matrix. It relates particularly to embedding microorganisms intended for the inoculation of leguminous plants in order to increase their nitrogen-fixing potential, and of non-leguminous plants in order to improve their nutrition with different elements.

The principal forms of plant inoculation used today are wet peat or peat granules. Such inoculums are applied to the soil or to the seeds with various coatings.

It is also known to employ particles of cellulose on which there are fixed bacteria and a culture medium, such as in U.S. Pat. No. 3,115,404, and granules of plaster (French Pat. No. 1,490,046), and of lignite.

It has also been proposed to employ a polymer gel, as in U.S. Pat. No. 4,155,737. One process for conducting enzymatic reactions employing microorganisms embedded in a polymer matrix is claimed in French Pat. No. 2,320,349, and it consists in continuously feeding a reactor containing the microorganisms, embedded in the polymer matrix, with a growth medium for said microorganisms containing the product to be treated. However, the process is applied, in fact, to a matrix of polymers of acrylic type.

However, a first difficulty resides in this latter proposal in the incorporating of the microorganism into the matrix of a polymer which is either biodegradable or non-polluting, without there being a decline in the activity of the microorganism. A second problem is that of the survival of the microorganism and its protection during transportation and storage. A third problem is the capability for the liberation of the embedded microorganism in order to permit its dispersion into the medium, and possible suitability for the grafting of additives. It is also necessary, of course, to assure penetration of the medium through the plant roots. Finally, sight must not be lost of the fact that the final product obtained must still be of sufficiently low cost.

None of the prior art solutions succeeds in simultaneously overcoming all of these problems.

It is, therefore an object of the present invention to provide new means of embedding microorganisms into a polymer matrix which overcomes the problems which have plagued the prior art.

It is also an object of the present invention to provide new means of embedding microorganisms into a problem matrix to be used for inoculating leguminous and non-leguminous plants.

It is a further object to provide the novel products produced by the novel process of the invention.

Other objects will be apparent to those skilled in the art from the present description.

GENERAL DESCRIPTION OF THE INVENTON

By the present invention it has now been discovered that a satisfactory solution can be obtained by employing as support a matrix having a base of at least one polymer selected from the group of polysaccharides, wherein the said polymer is subjected to an at least partial cross-linking treatment.

In the present invention there is understood by an at least partial cross-linking treatment, a treatment capable of modifying the structure of the polysaccharide, such as a heat treatment, treatment by a metal salt, or synergism by means of another polymer, and preferably with another polysaccharide.

The polymer advantageously has a base of a heteropolysaccharide of high molecular weight, obtained by fermentation of a carbohydrate by a microorganism of the genus Xanthomonas or Arthrobacter, or fungi of the genus Sclerotium.

One may also use polymers obtained from natural or biosynthetic gums of different origin, e.g., seaweed (alginates, carrageenan, agar), plant exudates (gums such as karaya, tragacanth, arabic), and seeds (guar, carob).

The bacterial concentration in the preparation can be increased by first centrifuging the culture medium, then again forming a suspension of the bacterial sediment in a small volume, and introducing it into the polysaccharide solution.

The microorganism or microorganisms may be added in accordance with various methods of operation which include, first of all, preparing a culture medium which is seeded with the microorganism and then adding this culture medium, or the microbic suspension obtained by centrifuging, to the polysaccharide solution and forming a gel by cooling.

In practice, in accordance with a first embodiment, a polysaccharide solution is first of all formed at an elevated temperature and then cooled to a temperature on the order of 40°–45° C., to which solution the culture medium containing the microorganism or the microbic suspension is added, followed by cooling, so as to form the gel.

In accordance with another embodiment, the culture medium or the microbic suspension is added separately to each polysaccharide solution under the same temperature conditions, followed by mixing and cooling to form the gel.

As stated above, a metal salt may also be used, such as an iron or aluminum salt, whether or not complexed by a polyol, to form a gel of the polysaccharide.

Furthermore, the polysaccharide can be dissolved in the culture medium, in particular at room temperature, and the cross-linking formed in situ.

The microorganisms in accordance with the invention are, preferably, of the genus Rhizobium.

The gel obtained can be kept for several weeks in the cold, at a temperature of about 4° C., in a physiological sodium chloride solution. However, it is advantageous to effect a drying of the gel. As stated previously, the microorganisms must not be destroyed, and it is known that the microorganisms are generally very sensitive to heat.

Drying, per se, is lengthy and leads to a dry film which is readily friable and which can be crushed without difficulty.

In accordance with the present invention, there is preferably added to the gel a porous substance of high water absorption capacity, such as natural or synthetic silica, silico-aluminates, cellulose, etc., at a pH close to about 7, and under a temperature sufficiently low not to destroy the microorganism, such as in the order of about 20°–30° C.

The shaping can be effected in various ways.

In accordance with a first embodiment, the gel is dried and then crushed fine, and a substance such as silica is added, whereupon it is homogenized. The powder thus obtained can then be formed as desired, such as in the shape of pellets, etc.

In accordance with another embodiment, the wet gel and the substance such as silica are introduced into a mixer or kneader and then, after kneading, the mixture is either spread out and dried directly until the loss of water corresponds to 50 percent of its weight, obtaining a powder having a residual water content of about 70 percent, or the mixture is introduced into an extruder and the granulates obtained are dried at room temperature until obtaining also a loss of water of about 50 percent.

In all cases, there is obtained a product in the form of powder, granulates, or pellets, which lend themselves to easy handling and good packing.

As previously stated, the heteropolysaccharide in accordance with the invention is of high molecular weight.

Representative strains of bacteria or fungi which can be used for the production of these heteropolysaccharides include, for instance, *Xanthomonas begoniae, Xanthomonas campestris, Xanthomonas carotae, Xanthomonas hederae, Xanthomonas incanae, Xanthomonas malvacearum, Xanthomonas papavericola, Xanthomonas phaseoli, Xanthomonas pisi, Xanthomonas vitians, Xanthomonas vasculorum, Xanthomonas vesicatoria, Xanthomonas pelargonii, Arthrobacter stabilis, Arthrobacter viscosus, Sclerotium glucanicum, Sclerotium rolfsil,* etc.

If an embodiment contemplated within the scope of the present invention makes a purification of the polysaccharide desirable, one can use for this purpose methods known in the prior art, consisting, for instance, of subjecting the fermented wort or the aqueous gel reconstituted from the heteropolysaccharide extracted from the wort to centrifuging operations over diatomaceous earths or to the action of enzymes of the protease type (see U.S. Pat. No. 3,729,460).

The microorganism is added in simple fashion to a conventional culture medium having a base of mannitol and yeast extract.

The process of the present invention can be used for other agricultural applications employing both bacteria and yeasts or fungi having the purpose of enriching the soil in microorganisms in order to favor:
 the detoxification of the soil;
 the oxidation or reduction of iron, sulfur, Mn, etc.;
 the fixing of free or symbiotic atmospheric nitrogen;
 the mineralizing of the nitrogen;
 the hydrolysis of cellulose and pectin;
 the solubilizing of phosphates; and
 the dislocating of the silicates, etc.

These microorganisms can be added alone or in the form of mixtures of several genera or species:
 Example: Rhizobium + yeasts + mycorrhizas.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

In a first series of examples, one operates under the following conditions:

The culture medium (with amounts expressed in terms of grams per liter) is formed of the medium YEM=yeast extract, mannitol [Wacek, T. J., Brill, W. J., *Crop Science,* 16, 519–523 (1976)].
Mannitol 5.0–10.0; Yeast Extract Difco 0.5–1.0;
$K_2HPO_4$ 0.5; $MgSO_4.7H_2O$ 0.2;
$FeCl_3$ 0.004; NaCl 0.2;
pH adjusted to 7.0 with N HCl;
$H_2O$ distilled to provide 1000 ml.;
Sterilization: 20 minutes at 120° C.
Liquid Culture
Medium: YEM
Conditions: 100 ml. medium in a 300 ml. Erlenmeyer flask stoppered with a polyurethane stopper, sterilization for 20 minutes at 120° C.;

Seeding by culture used directly after incubation (or possibly kept at +4° C.) of *Rh. japonicum* strain G3 USDA 3I1-b 138 collection INRA 7, Rue Sully 21000, Dijon, France), on YEM agar, or preferably, by an intermediate liquid inoculum culture;

Incubation 4 to 5 days at 28° C., on an agitation table turning at 140 rpm;
 eccentricity of the plate: 25 mm.;
The population of the culture is between $1–3.0 \times 10^9$ organisms/ml.; the pH is 7–7.2.

Preparation of the Gel of Polysaccharides with Rhizobium Embedded

Polysaccharides used:
Heteropolysaccharide of the anionic type, resulting from the fermentation of carbohydrates by a microorganism of the genus Xanthomonas, $MW > 2 \times 10^6$, which will be referred to hereinbelow as product "A," or simply "A."

Carob seed flour = polysaccharide formed of units of $\beta$-D-manno-pyranosyl (bounds 1→4) one out of four or five being substituted in $C_6$ by an $\alpha$-D-galactopyranosyl, $MW = 3.1 \times 10^5$, which will be hereinafter referred to as product "B," or simply "B."

Manner of Operation

Manner of Operation No. 1:
The concentrations are given for the preparation of 120 g. of gel:
 there are mixed, as a powder, 0.6 g. of "A" + 0.6 g. of "B";
 100 ml. of distilled water are introduced at a temperature of 70°–80° C.;
 the mixture of powder "A" + "B" is poured in with agitation;
 agitation is continued at a temperature between 70° and 80° C. for 20 to 30 minutes;
 the temperature is reduced to between 40° and 45° C.;
 20 ml. of the liquid culture are added;
 the mixture is agitated in order to homogenize it; the mixture is cooled; the gel is formed with greater or lesser rapidity depending on the cooling temperature.

Manner of Operation No. 2:
The concentrations are given for the preparation of 300 g. of gel:
 100 ml. of distilled water are fed at a temperature of 70°–80° C.;
 1.5 g. of "A" is added; it is left at this temperature for 20 to 30 minutes and then reduced to between 40° and 45° C.;
 one proceeds in the same manner, replacing "A" by 1.5 g. of "B";

when the two solutions are at 40°–45° C., under agitation there are added 50 ml. of the liquid culture to each;

the mixture (culture+"B") is then poured with agitation into the mixture (culture+"A");

cooling is effected.

As previously, there is obtained a gel of a rubberlike consistency and the survival rate of the Rhizobium is close to 100 percent.

Gel No. 1, 6 g. of gel corresponding to 1 ml. of culture;

Gel No. 2, 3 g. of gel corresponding to 1 ml. of culture.

It is noted that whatever the manner of preparation, the gel can be kept for several weeks at 4° C. in sterile physiological water.

Drying of the Gel

Manner of Procedure

1. Gel without additive: The gel is crushed so as to obtain a maximum thickness of 5 mm.; the drying is effected in 16–20 hours at a temperature of between 24°–29° C.; the loss of water is 98.5 percent on the average.

2. Gel with additive: Precipitated silica (silica 1).

There is added to the gel 40 percent of its weight of precipitated silica of BET surface substantially equal to 250 square meters per gram, oil uptake 320 cc./100 g., CTAB 170 square meters per gram, the silica is mixed with the gel until obtaining a powder of slightly moist and homogeneous appearance.

The measurements are carried out in accordance with the following methods:

CTAB surface: Outer surface by adsorption of cetyl trimethyl ammonium bromide at pH 9 in accordance with the method described by Jay, Janzen and G. Kraus, in *Rubber Chemistry and Technology*, 44, pages 1287–1296 (1971).

The specific BET surface is determined in accordance with the method of Brunauer, Emmett-Teller, described in the *Journal of the American Chemical Society*, Vol. 60 page 309 (February 1938).

Oil uptake: dioctylphthalate.

This "powder" is spread out so as to obtain a layer of a thickness of between 5 and 10 mm., and thereupon placed to dry at a temperature between 24°–29° C., until the loss of water corresponds to 50–55 percent of the weight of the mixture. There is then obtained an apparently dry powder which is easy to handle and the residual water content of which is 50–70 g./100 g. of silica added. Under these conditions, the drying takes 7–8 hours.

Results

Viability of *Rhizobium japonicum* After Drying

In order to show the protective effect of the gel on the survival of the microorganism, the silica is added either to the culture alone or to the culture containing 10 grams per liter of heteropolysaccharide or to gels prepared in accordance with the invention, in an amount of 40 g./100 g. of the culture or mixture in question.

These preparations, which have the appearance of a "wet powder," are dried for variable periods of time in such a manner that the residual water content of the powders ranges between 150 and about zero percent (i.e., desiccation). The results obtained are set forth in Table I, below.

Parallel to this, the results obtained with the dried gel without additive or in the presence of an inert additive (sand or powdered glass) are indicated.

The viability of the microorganism is determined by the conventional technique of dilution suspensions spread out on YEM agar medium.

It is also possible to obtain a powder ready for use by mixing the gel with 65–100 percent of its weight of silica.

TABLE I

Viability of Rh. japonicum during drying
(log number of organisms referred to 1 ml. of culture)

| $H_2O$ residual (% additive*) Treatment | 140 | 100 | 50 | 10 | Dessiccation 10–20 hrs. | 25–30 hrs. |
|---|---|---|---|---|---|---|
| Culture - silica 1 | 8.0 | 7.9 | 7.6 | 6.4 | 5.0 | 3.6 |
| Culture + product in accordance with the invention and silica | 8.7 | 8.6 | 7.9 | 6.7 | 5.6 | 4.7 |
| Gel No. 2 + silica 1 | 9.0 | 8.8 | 8.7 | 7.9 | 7.4 | 6.9 |
| Gel + cellulose | | | | 8.3 | 7.3 | 5.3 |
| Gel + powdered glass | | | | | 7.8 | 7.6 |
| Gel + sand | | | | | 8.3 | |
| Gel (No. 2) | | | | | 8.3 | |
| Gel (No. 1) | | | | | 7.5 | |

*Additive = 40% of the weight of the culture of gel (except in the case of sand = 60%).

It is observed that the process of the invention shows after drying:

a protective effect of the gel, and a good survival of the microorganism in the gel, whether or not an inert substance has been added.

However, the addition of silica in this case is compatible with a good survival of the microorganism only if the residual $H_2O$ content is above a threshold on the order of 50 percent of the weight of additive; see Table II, below.

In general, the percentage of additive may vary from 10 to 120 percent depending on the additive in question, but it is preferably on the order of 40 percent.

TABLE II

Viability of Rh. japonicum during storage at 28° C. as a function of the initial content of residual water (mixture gel + silica, results expressed in log number of organisms)

| Residual $H_2O$ initial (% silica) | Log number of organisms (referred to 1 ml. of culture) | |
|---|---|---|
| | time 0 | after 13 days at 28° C. |
| 155 | 8.5 | 8.4 |
| 78 | 8.5 | 7.4 |
| dessiccation | 6.8 | 3.0 |

Viability of *Rhizobium japonicum* During Storage at 28° C.

The dehydrated samples (gels "as is" or with inert additives) or samples containing a certain amount of water (gel+silica) are kept at 28° C., in a stoppered bottle for variable periods of time.

The results obtained:

on dehydrated gel;

on the gel+silic containing 56 to 81 percent residual water, are shown in Table III, below.

There is noted a satisfactory survival of the microorganism for at least 60 to 70 days.

TABLE III

Viability of Rh. japonicum during storage at 28° C.
(log number of organisms)

| Sample | Residual $H_2O$ | Number of days storage 28° C. | Number of tests | Log number organisms (referred to 1 ml. of culture) mean | extreme values |
|---|---|---|---|---|---|
| Gel | <1 | 0 | 9 | 8.0 | 7.2–8.6 |
| (No. 1 or 2) | | 7–14 | 6 | 7.3 | 6.4–8.2 |
| | | 17–25 | 3 | 7.5 | 6.9–7.9 |
| | | 34–35 | 3 | 6.6 | 5.6–7.7 |
| | | 68 | 2 | 6.9 | 6.7–7.1 |
| Gel | 56–81 | 0 | 12 | 8.6 | 8.5–8.7 |
| (No. 1 or 2) | | 4–7 | 5 | 8.1 | 7.2–8.6 |
| + silica 1 | | 9–15 | 8 | 7.4 | 6.4–8.5 |
| | | 21–25 | 5 | 7.6 | 6.9–8.1 |
| | | 45 | 1 | 5.9 | — |
| | | 60 | 1 | 8.3 | — |

The infectivity of Rh. japonicum was checked on Glycine max. variety AMSOY 71 in synthetic agar medium without nitrogen in accordance with a procedure derived from that described by Vincent, J. M., 1970.

The number of nodules formed from an inoculum formed by the culture or the mixture (gel+silica) dried and stored at 28° C. (for 4–27 or 60 days) is 56 and 55, respectively, and, therefore, there is preservation of the viability and infectivity of the microorganisms in the inoculums prepared in this manner.

Furthermore, the present invention permits shaping in pellets or granulates.

1. Gel without additive: After drying, the gel is finely crushed, silica added and then homogenized. The powder thus obtained is pelleted without difficulty in a pelleter of type ARCA; there are then obtained dry pellets of cylindrical shape ($\phi=3$ mm., height=3 mm.).

2. Gel with additive: The wet gel and then the silica are introduced into a mixer of the Kustner type and kneaded for 5 to 10 minutes; the mixture thus obtained is treated in two different ways;

(a) either spreading and direct drying of the mixture between 24°–29° C., until the loss of water corresponds to 50 pecent of its weight and then shaping in a pelleter, or (b) preferably, introduction of the mixture into an extruder of the Alexanderwerk type, obtaining wet granulates ($\phi=3$ mm., height=3 mm.); these granulates are dried very rapidly at room temperature up to a loss of 50 percent of their weight; the drying is accelerated by passing a flow of air over these preparations.

In all cases, there are obtained resistant granulates which lend themselves easily to handling or conditioning.

Furthermore, cross-linking can be effected by a metallic salt of iron or aluminum, complexed or not by a polyol (sorbitol, glycerol). This metallic salt solution is added to a culture medium containing 5 to 15 g./l. of the same heteropolysaccharide as previously.

In the case of aluminum, the sulfate or nitrate and preferably chloride, were used. It was thus possible to obtain fibers with loss of water by syneresis of between 80 and 90 percent of the total weight initially used.

In a second series of examples, preparations having a base of carrageenan (kappa) and alginate were produced.

Preparation of the Gels with Rhizobium Embedded Polysaccharides Used

Kappa-carrageenan: Galactose units, sulfated to a greater or lesser extent, alternately bound in 1–3 or 1–4 (D-galactopyranose 4 sulfate unit bond 1→3+3–6 anhydro D-galactopyranose bond 1→4).

Sodium alginate: Copolymer of units of $\beta$-D-(1→4) manno-pyranosyluronic acid and $\alpha$-L-(1→4) gulopyranosyluronic acids, the ratio of which varies as a function of the type of algae used; MW=32–200·10³ depending on the degree of polymerization.

Manner of Procedure

Preparation with base of Kappa-carrageenan (Kc)

The concentrations are given for the preparation of 160 g. of gel.

Manner of Operation No. 1 (Kc gel):

110 ml. of distilled water are brought to a temperature of 70°–80° C.

1.6 g. of Kc powder are added with agitation, left under agitation at a temperature of about 70° C. until complete dissolution is obtained (about 20 minutes). The temperature is reduced to about 45° C. 50 ml. of the liquid culture are added with agitation until obtaining a homogeneous mixture.

The pH of the mixture obtained is then between 7 and 7.5. The gel is formed with greater or lesser speed depending on the cooling temperature: 60–90 minutes at room temperature.

Manner of Operation No. 2 (Kc-Ca gel):

One proceeds in the same manner as previously, but at the time of adding the liquid culture one adds to the latter 0.8 g. of $CaCl_2.2H_2O$.

The pH is then between 6.5 and 7.0 and the gel is formed in 5 to 15 minutes at room temperature.

Manner of Operation No. 3 (Kc-Gc gel):

1.2 g. of Kc powder and 0.4 g. of carob bean flour are mixed. 110 ml. of distilled water are brought to 70°–80° C. The mixture of powders is poured in with agitation and left under agitation between 70°–80° C. for about 20 minutes. The temperature is reduced to about 45° C. 50 ml. of the liquid culture are added with agitation so as to obtain a homogeneous mixture.

The pH of the mixture is between 7.2 and 7.5 and the gel is formed in 30–40 minutes at room temperature.

Preparations Having a Base of Sodium Alginate

The concentrations are given for the preparation of 100 g. of gel. All the operations are carried out at room temperature, with agitation.

Manner of Operation No. 4 (ALG-Ca gel):

1 g. of sodium alginate (high viscosity alginate S 800, Etablissements Francois) is added to 80 ml. of liquid culture. After dissolving and homogenization, 20 ml. are added of 6 g./l. solution of $CaSO_4.2H_2O$.

The pH of the mixture is between 7.0 and 7.5. The gelation is practically instantaneous.

Manner of Operation No. 5 (ALG-Ca-PO4 gel):

One proceeds as previously, but the 20 ml. of $CaSO_4.2H_2O$ solution contains furthermore $Na_2HPO_4$ in a concentration of 1 g./l.

The pH is close to 7.5. The gelation is delayed 5 to 10 minutes by the addition of $Na_2HPO_4$.

These manners of operation are not limitative. Gels with slower or faster setting can be obtained by modifying the concentration of the polysaccharides and the salts, the temperature of preparation, and the nature and valence of the cations used.

The viability of the microorganism in all these non-dehydrated preparations is 100 percent.

Drying of the Gel

The drying procedure is identical to that of the preceding examples. Different drying additives are used:

synthetic silica: (2) CTAB 90 m²/g., BET 200 m²/g.—oil uptake 346 cc./100 g.

synthetic silica: (3) CTAB 90 m²/g., BET 200 m²/g.—oil uptake 340 cc./100 g.

natural silica CLARCEL FLO silica (4) having a base of perlite (produced by CECA)—oil uptake 350 cc./100 g.

Results

Viability of embedded *Rhizobium japonicum* after drying and storing at 28° C.

Gel Without Additive

The influence of various polysaccharides was compared, alone, in mixture, or with addition of salts. With respect to the survival of two strains of *Rhizobium japonicum* [strains $G_3$ (USDA 3I1 b 138) and $G_2SP$ (USDA 3I1 b 125) collection INRA Dijon, France] after embedment, desiccation and storage at 28° C. The results are set forth in Table IV, below.

TABLE IV

| Dehydrated gel | Weight dried gel corresponding to 1 ml. of culture (mg.) | Viability (log number of organisms referred to 1 ml. of culture) | | | |
|---|---|---|---|---|---|
| | | Strain $G_3$ | | Strain $G_2SP$ | |
| | | t = 0 | t = 60 days | t = 0 | t = 50 days |
| gel 2[(1)] | 40 | 8.9 | 8.7 | 7.7 | 0 |
| Kc | 38 | 8.6 | 7.6 | 6.7 | 0 |
| Kc—Ca | 66 | 8.4 | 6.5 | — | 0 |
| Kc—Gc | 36 | 9.2 | 8.7 | 6.7 | 6.7 |
| ALG—Ca | 27 | 9.1 | 8.5 | 8.1 | 8.1 |
| ALG—Ca—PO₂ | 22 | 8.8 | 8.1 | 7.7 | 7.2 |
| PPA[(2)] | 80 | 7.8 | 5.5 | 6.1 | 0 |

[(1)]Xanthane gum gel + carob bean flour
[(2)]Polyacrylamide gel [described in U.S. Pat. No. 4,155,737]

It appears that for a given species of microorganism the resistance to desiccation may be different depending on the strain in question. The type of polymer serving for the embedment plays an important role.

Gel Without Additive

The gel is treated with 40 percent of its weight either with precipitated silica or natural silica (CLARCEL FLO having a base of perlite). After mixing, evaporation is effected until obtaining a powder whose residual water content is between zero and 75 g. per 100 g. of additive. The samples are kept preferably in hermetically sealed bags or bottles at a temperature of 28° C.

Influence of the Additive on the Survival of the Rhizobium

A gel having a base of xanthan gum+carob bean flour is treated with synthetic or natural silica, dried until the residual water content is between 50 and 70 percent. The viability of *Rh. japonicum* (strain $G_3$) is closed to 100 percent after 8 months of preservation at 28° C. for gel+additive, while it is practically zero for the dehydrated gel without additive. The results are set forth in Table V, below.

TABLE V

| Number of days storage at 28° C. | Dried powder gel 2[(1)] | Viability (log number of organisms referred to 1 ml. of culture) powder with 50-70% residual water | | |
|---|---|---|---|---|
| | | gel 2 + silica 2 | gel 2 + silica 3 | gel 2 + natural silica |
| 0 | 8.7 | 8.7 | 9.2 | 9.2 |
| 30-40 | 7.9 | 8.8 | 9.0 | 9.4 |
| 80 | 7.0 | | 8.8 | |
| 120 | 6.5 | | 9.0 | |
| 160-175 | 5.5 | 8.3 | 8.9 | |
| 210-220 | 4.8 | 8.2 | 9.1 | |
| 250 | 4.0 | 7.4 | | |
| 300 | <3 | | | 9.2 |

[(1)]mean values of 10 tests

Influence of the Nature of the Additive and of the Residual Water Content on the Survival of *Rh. japonicum* (Strain $G_3$)

The gel is treated with silica 1, 2, or 3, or CLARCEL FLO, and the mixtures obtained are dried depending on the individual case to a residual water content of between zero and 75 percent. The results are set forth in Table VI, below.

TABLE VI

| Number of days storage at 28° C. | Gel (2) +additive | Residual H₂O (% additive) | | | | | |
|---|---|---|---|---|---|---|---|
| | | 75 | 50 | 36 | 25 | 10 | 0 |
| 0 | silica 1 | 8.7 | 8.7 | | | 7.9 | 6.9 |
| | silica 2 | 8.8 | | 9.1 | | | 8.3 |
| | silica 3 | 9.1 | | 9.1 | | | 8.3 |
| | silica 4 | 9.4 | 9.2 | 9.0 | 9.4 | 8.8 | 8.5 |
| 12-23 | silica 1 | 7.8 | 7.4 | | | <3 | <3 |
| | silica 2 | 8.7 | | 8.5 | | | 7.4 |
| | silica 3 | 8.8 | | 8.6 | | | 7.4 |
| | silica 4 | 9.4 | 9.4 | 9.6 | 9.2 | 8.4 | 4.6 |
| 40-62 | silica 1 | 6.6 | | | | | |
| | silica 2 | 8.5 | | 8.5 | | | 6.7 |
| | silica 3 | 8.6 | | 8.4 | | | 6.3 |
| | silica 4 | 9.3 | 9.6 | 9.6 | 9.4 | 8.8 | 3.8 |
| 220-300 | silica 1 | 3 | | | | | |
| | silica 2 | 7.4 | | | | | |
| | silica 3 | 9.1 | | | | | |
| | silica 4 | | 9.2 | 9.4 | 8.8 | 8.6 | <3 |

While the additive consisting of silica 1 permits only a limited survival of Rhizobium in time, even when the residual water content is high (about 75 percent), on the other hand, with additives 2 and 3, the survival of the microorganism is 100 percent even when the residual water content is between 10 and 30 percent.

Protective Effect of the Additive During Storage at 28° C.

Four strains of Rh. leguminosarum (strains PD12, 1007, FH13, FH20SI collection, INRA, 7 rue Sully—21000Dijon, France) which are sensitive to desiccation were embedded in gel of xanthan gum+carob bean flour (2) and the inoculum thus prepared was treated with silica of high retention of water (1 or 2). After drying (to 75 percent residual water), the samples were kept in a stoppered flask at 28° C. The results are set forth in Table VII, below.

TABLE VII

| Strain Rh. leguminosarum | Viability (log number of organisms referred to 1 ml. of culture) | | | | | |
|---|---|---|---|---|---|---|
| | Gel 2 dehydrated | | Gel 2 + silica 1 | | Gel 2 + silica 2 | |
| | 0 | 30 days | 0 | 30 days | 0 | 30 days |
| PD 12 | 8.2 | <5 | 8.6 | 7.3 | 8.6 | 8.3 |
| 1007 | 8.5 | 6.6 | 8.6 | 5.8 | 9.0 | 9.1 |
| FH 13 | 8.7 | <5 | 8.9 | 7.5 | 8.4 | 8.8 |
| FH 20S1 | 8.9 | 6.3 | 8.4 | 7.0 | 8.7 | 8.6 |

(1)culture medium (g./l.): saccharose 10-$K_2HPO_4$ 0.5 - $MgSO_4.7H_2O$ 0.2-NaCl 0.2-$FeCl_3$ 0.004 - Yeast Extract Difco 1 - $CaCO_3$ 2 to 5.

It is only in the preparations to which silica 2 is added that the viability is 100 percent after 30 days of preservation.

The preceding examples show the great importance of the present invention. Obviously, the inoculation of the grains or soil can be effected in any known manner, such as, for instance, that described in the description of the prior art.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process for producing a dry, stable, storable, and biologically-active product of microorganisms embedded in matrix of a polymer gel comprising the steps of forming a polymer gel by combining at least one polymer selected from the group of the polysaccharides with a biologically-active microorganism-containing composition and at least partially cross-linking said polymer, said cross-linking embedding said microorganisms in the matrix of said polymer gel; and drying said polymer gel, said drying not converting the microorganisms embedded in said polymer gel to a dormant or latent state.

2. A process for producing a dry, stable, storable, and biologically-active product in accordance with claim 1, wherein the partial cross-linking of said polymer is effected by heat treatment.

3. A process for producing a dry, stable, storable, and biologically-active product according to claim 1, wherein the partial cross-linking of said polymer is effected by action of a metallic salt.

4. A process for producing a dry, stable, storable, and biologically-active product according to claim 3, wherein the polysaccharide is dissolved at room temperature in a culture medium containing the microorganism or a microbic suspension obtained by centrifuging said microorganism-containing culture medium and the cross-linking is formed in situ.

5. A process for producing a dry, stable, storable, and biologically-active product according to claim 1, wherein the said partial cross-linking is provided by another polymer.

6. A process for producing a dry, stable, storable, and biologically-active product according to claim 5, wherein said other polymer is another polysaccharide.

7. A process for producing a dry, stable, storable, and biologically-active product according to claim 1, wherein the said polymer has a base of a heteropolysaccharide of high molecular weight, obtained by fermentation of a strain selected from the group consisting of Xanthomonas Arthrobacter, and fungi belonging to the genus Sclerotium.

8. A process for producing a dry, stable, storable, and biologically-active product according to claim 7, wherein said polymer also comprises at least one other polysaccharide selected from the group consisting of carob bean flour and gums of natural origin.

9. A process for producing a dry, stable, storable, and biologically-active product according to claim 7, wherein the said partial cross-linking is formed by cooling.

10. A process for producing a dry, stable, storable, and biologically-active product according to claim 7, wherein at least one polysaccharide solution is first prepared at an elevated temperature, its temperature is reduced to 40°–45° C., and a culture medium containing the microorganism or a microbic suspension obtained by centrifuging said microorganism-containing culture medium is added, and the said partial cross-linking is formed by cooling.

11. A process for producing a dry, stable, storable, and biologically-active product according to claim 10, wherein a portion of said culture medium or microbic suspension is added separately to each polysaccharide solution.

12. A process for producing a dry, stable, storable, and biologically-active product according to claim 1, wherein the microorganism is of the genus Rhizobium.

13. A process for producing a dry, stable, storable, and biologically-active product according to claim 1, wherein prior to the drying a substance of high water absorption capacity is added to the gel, whereby the residual water content of the gel plus absorbent is greater than 50 percent by weight based on the absorbent.

14. A process for producing a dry, stable, storable, and biologically-active product according to claim 12, wherein the substance added consists of silica and the residual water content of the mixture of gel plus silica is 50-70 g/100 g of silica.

15. A process for producing a dry, stable, storable, and biologically-active product according to claim 13, wherein the pecentage of the substance added is 10–120 percent by weight based on the gel.

16. A process for producing a dry, stable, storable, and biologically-active product according to claim 13, wherein the substance added consists of a precipitation silica of BET surface equal to 200 $m^2/g$, CTAB surface equal to 90 $m^2/g$ and dioctylphthalate oil uptake equal to 340–346 cc/100 g.

17. A process for producing a dry, stable, storable, and biologically-active product according to claim 1, wherein said polymer gel is dried at ambient temperature.

18. A process for producing a dry, stable, storable, and biologically-active product according to claim 1, wherein said polymer gel is dried to a water loss of about 50 percent.

* * * * *

UNITED STATES PATENT AND TRADEMARK OFFICE
CERTIFICATE OF CORRECTION

PATENT NO. : 4,434,231
DATED : February 28, 1984
INVENTOR(S) : Gerard Jung

It is certified that error appears in the above-identified patent and that said Letters Patent is hereby corrected as shown below:

Column 6, line 64      "silic" should be --silica--

Column 9, line 26,     "3I1 b 125" should be --331 b 135--

Column 9, Table IV,    "ALG-Ca-$PO_2$" should be --ALG-Ca-$PO_4$--

Column 10, line 52,    "12-23" should be --12-28--

Signed and Sealed this

Twentieth Day of May 1986

[SEAL]

Attest:

DONALD J. QUIGG

Attesting Officer      Commissioner of Patents and Trademarks